US00PP27442P2

(12) United States Plant Patent
Kibbe et al.

(10) Patent No.: US PP27,442 P2
(45) Date of Patent: Dec. 6, 2016

(54) STRAWBERRY PLANT NAMED 'DRISSTRAWFORTYEIGHT'

(50) Latin Name: *Fragaria×ananassa*
Varietal Denomination: DrisStrawFortyEight

(71) Applicant: DRISCOLL STRAWBERRY ASSOCIATES, INC., Watsonville, CA (US)

(72) Inventors: Esther Kibbe, Alden, NY (US); Philip J. Stewart, Watsonville, CA (US); Mary M. Calkins, Plant City, FL (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 0 days.

(21) Appl. No.: 14/756,125

(22) Filed: Aug. 4, 2015

(51) Int. Cl.
*A01H 5/08* (2006.01)

(52) U.S. Cl.
USPC ..... Plt./209

(58) Field of Classification Search
USPC ..... Plt./208, 209
See application file for complete search history.

*Primary Examiner* — Susan McCormick Ewoldt
(74) *Attorney, Agent, or Firm* — Morrison and Foerster LLP

(57) ABSTRACT

A new and distinct variety of strawberry plant named 'DrisStrawFortyEight' particularly characterized by having medium-sized, medium red fruit, a globose—semi-upright plant habit, and very early harvest maturity, is disclosed.

3 Drawing Sheets

Genus and species: *Fragaria×ananassa.*
Variety denomination: 'DrisStrawFortyEight'.

BACKGROUND OF THE NEW PLANT

The present invention relates to a new and distinct strawberry variety designated 'DrisStrawFortyEight' and botanically known as *Fragaria×ananassa*. This new strawberry variety was discovered in Hillsborough County, Fla. in November 2010 and originated from a cross between the proprietary female parent 'DrisStrawNineteen' (U.S. Plant Pat. No. 23,148) and the proprietary male parent '126R399' (unpatented). A single plant was selected and asexually propagated via tissue culture and vegetative cuttings in Shasta County, Calif. in 2010.

'DrisStrawFortyEight' underwent further testing in Hillsborough County, Fla. from 2010-2015. The present invention has been found to retain its distinctive characteristics through successive asexual propagations via stolons and tissue culture.

Plant Breeder's Rights for this variety have not been applied for. 'DrisStrawFortyEight' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Hillsborough County, Fla.

1. Medium-sized, medium red fruit;
2. Globose—semi-upright plant habit; and
3. Very early harvest maturity.

DESCRIPTION OF THE PHOTOGRAPHS

The accompanying color photographs show typical specimens of the new variety at various stages of development.

The colors shown are as true as can be reasonably obtained by conventional photographic procedures. The photographs were taken from seven-month-old plants.

DESCRIPTION OF THE NEW VARIETY

Figure 1:
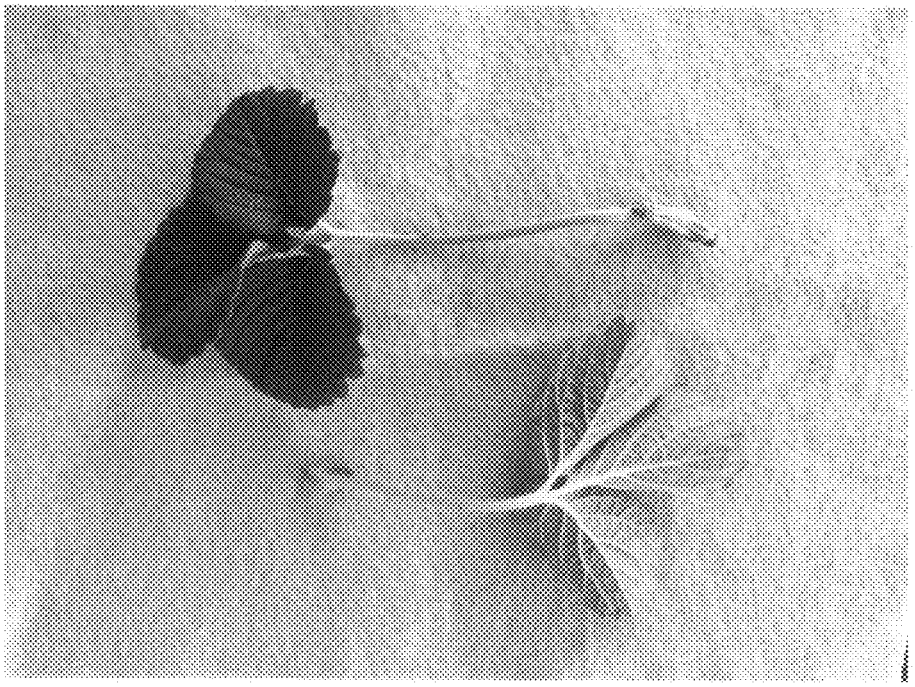
FIG. 1 shows upper and lower surfaces of the leaves of the plant with three leaflets.
Figure 2:
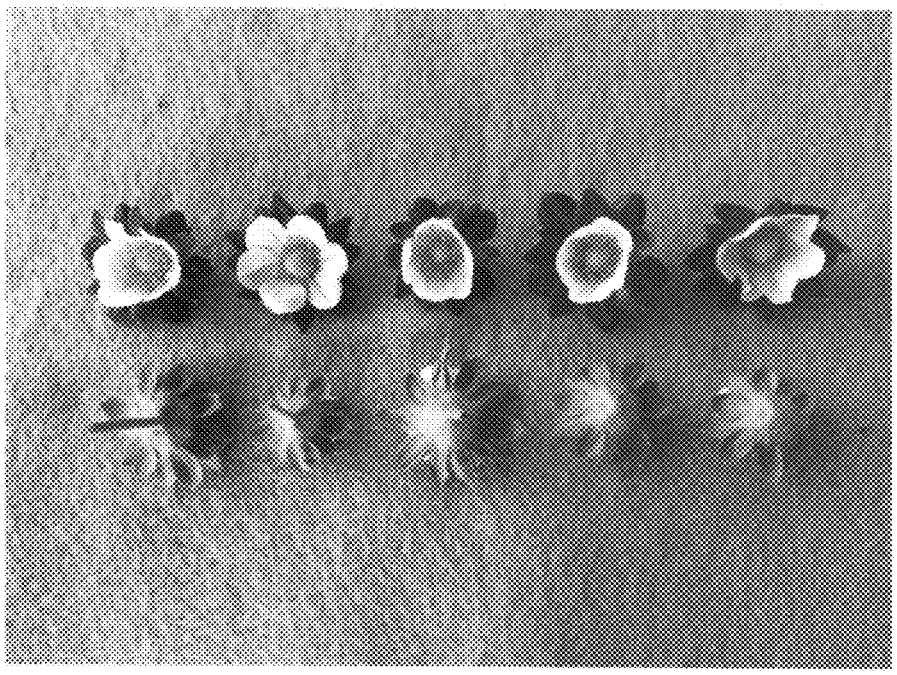
FIG. 2 shows both upper and lower surfaces of the flowers.
Figure 3:
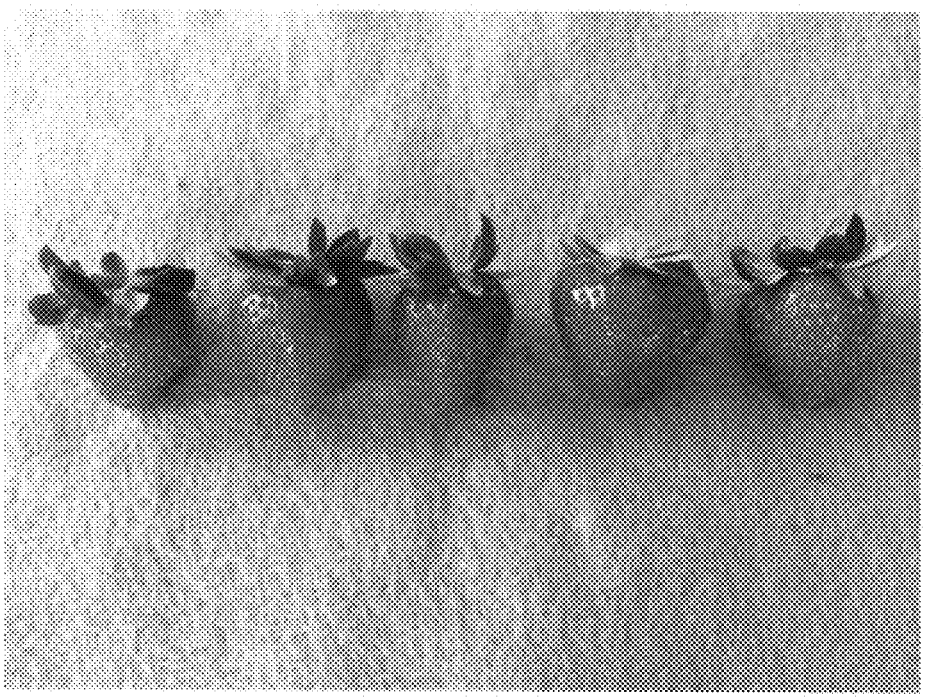
FIG. 3 shows the whole fruit.
Figure 4:
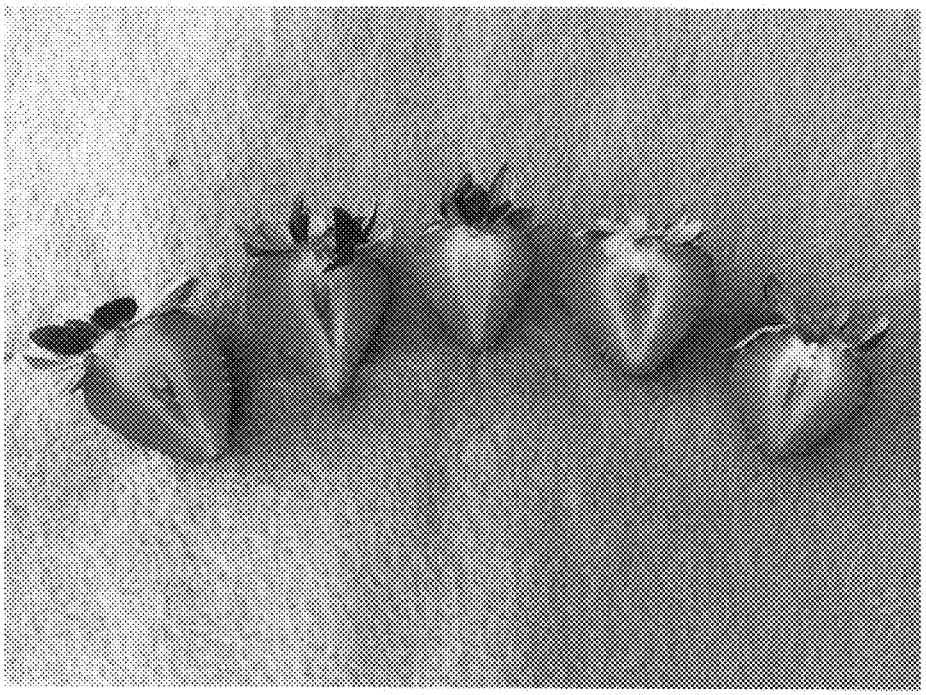
FIG. 4 shows the fruit in longitudinal cross-section.
Figure 5:
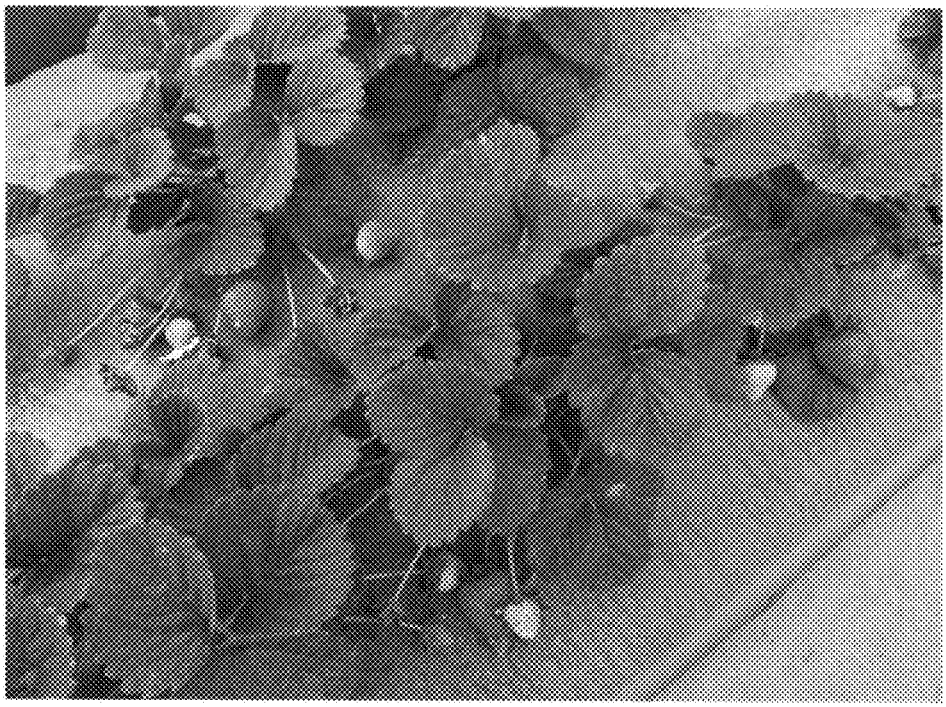
FIG. 5 shows the entire plant habit.

The following detailed descriptions set forth the distinctive characteristics of 'DrisStrawFortyEight'. The data which define these characteristics is based on observations taken in Hillsborough County, Fla. from 2010 to 2015. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortyEight' has not been observed under all possible environmental conditions. The botanical description of 'DrisStrawFortyEight' was taken from seven-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria x ananassa.*
*Common name.*—Strawberry.
*Denomination.*—'DrisStrawFortyEight'.

Parentage:
*Female parent*.—The proprietary variety 'DrisStrawNineteen' (U.S. Plant Pat. No. 23,148).
*Male parent*.—The proprietary variety '126R399' (unpatented).
Plant:
*Height*.—11.2 cm.
*Diameter*.—25.0 cm.
*Number of crowns/plant*.—3.
*Habit*.—Globose — semi-upright.
*Density of individual plant*.—Medium.
*Vigor* (*health and hardiness of plant*).—Weak.
Terminal leaflets:
*Size*.—Small. Length: 5.3 cm. Width: 5.6 cm. Length/width ratio: 1.0 (As long as broad).
*Number of teeth/terminal leaflet*.—19.
*Shape of teeth*.—Obtuse — serrate to crenate.
*Color*.—Upper surface: RHS 137A (Medium green). Lower surface: RHS 144B (Light yellow-green).
*Shape in cross section*.—Slightly concave.
*Blistering*.—Weak.
*Glossiness*.—Absent or weak.
*Number of leaflets*.—Three only.
*Shape*.—Orbicular.
*Base shape*.—Rounded.
*Apex descriptor*.—Rounded.
*Margin*.—Crenate.
*Margin profile*.—Flat (level with the leaflet blade).
*Variegation*.—Absent.
Petiole:
*Length*.—Short; 8.0 cm.
*Diameter*.—3.31 mm.
*Pubescence*.—Dense.
*Pose of hairs*.—Outwards — horizontal.
*Color*.—RHS 144B (Yellow-green).
*Bract frequency*.—0.
Petiolule:
*Length*.—6.05 mm.
*Diameter*.—2.14 mm.
*Color*.—RHS 144B (Yellow-green).
Stipule:
*Length*.—2.8 cm.
*Width*.—9.2 mm.
*Pubescence*.—Medium.
*Stipule anthocyanin coloration*.—Medium; RHS 32A (Medium orange-red).
Inflorescence:
*Position relative to foliage*.—Level.
*Number of flowers per plant*.—Medium; 3.1.
*Time of flowering* (*50% of plants at first flower*).—Very early; Late October to late March.
*Flower size*.—Medium.
*Flower diameter*.—21.88 mm.
*Petals*.—Shape: Orbicular. Apex: Rounded. Base: Concavo-convex. Margin: Entire. Spacing: Overlapping. Length: 9.88 mm. Width: 10.45 mm. Length/width ratio: 0.9 (As long as broad). Petal number per flower: 6. Color (upper surface): RHS NN155B (White).
*Calyx*.—Diameter: 30.80 mm. Diameter relative to corolla: Larger. Inner calyx diameter relative to outer: Same size. Insertion of calyx: In a basin — inserted. Pose of calyx segments: Reflexed — upwards. Size of calyx in relation to fruit: Same size. Adherence of calyx: Strong.
*Sepal*.—Shape: Elliptical. Apex: Convex. Margin: Entire. Length: 11.57 mm. Width: 6.45 mm. Sepal number: 12.
*Receptacle color*.—RHS 145A (Yellow-green).
*Stamen*.—Present. Anther color: RHS 13A (Yellow).
*Pedicel*.—Attitude of hairs: Slightly upwards.
Fruiting truss:
*Length*.—Medium; 18.6 cm.
*Diameter at base of truss*.—3.76 mm.
*Number of berries per fruiting truss*.—3.
*Attitude at first picking*.—Prostrate.
*Color at base of truss*.—RHS 144B (Yellow-green).
Fruit:
*Relative fruit size*.—Medium.
*Length*.—48.51 mm.
*Width*.—42.63 mm.
*Length/width ratio*.—1.1 (Longer than broad).
*Fruit hollow length*.—21.71 mm.
*Fruit hollow width*.—4.26 mm.
*Fruit hollow length/width ratio*.—5.1 (Longer than broad).
*Fruit hollow center* (*cavity*).—Medium.
*Fruit weight*.—25.3 g.
*Predominant fruit shape*.—Conical.
*Difference in shape between primary and secondary fruits*.—Slight.
*Evenness of fruit surface*.—Even or very slightly uneven.
*Fruit skin color*.—RHS 43A (Medium red).
*Evenness of fruit color*.—Even or very slightly uneven.
*Fruit glossiness*.—Medium.
*Achenes*.—Insertion of achenes: Level with surface. Coloration (sunward side of berry): RHS 60A (Red-purple). Coloration (shaded side of berry): RHS 151B (Yellow-green). Number per berry: 320. Weight (weight of achenes divided by total # seed): 0.0046875 g. Width of band without achenes: Narrow.
*Firmness of flesh* (*when fully ripe*).—Firm.
*Color of flesh* (*excluding core*).—RHS 34A (Orange-red).
*Color of core*.—RHS 31B (Light orange-red).
*Evenness of flesh color*.—Slightly uneven.
*Distribution of flesh color*.—Marginal and central.
*Sweetness*.—Medium.
*Acidity*.—Medium.
*Texture when tasted*.—Fine.
*Type of bearing*.—Partially everbearing — partially remontant.
*Harvest interval*.—Mid-November to late March.
*Harvest maturity*.—Very early.
*Production*.—356.7 grams per plant.
Disease and pest resistance:
*Tetranychus urticae*.—Susceptible.
*Botrytis fruit rot*.—Susceptible.
Stress resistance:
*High temperatures*.—Moderately resistant.
*Wind*.—Moderately susceptible.
*High pH*.—Resistant.

COMPARISON WITH PARENTAL AND COMMERCIAL VARIETIES

When 'DrisStrawFortyEight' is compared to the female parent 'DrisStrawNineteen' (U.S. Plant Pat. No. 23,148), 'DrisStrawFortyEight' has a globose—semi-upright plant habit and medium red fruit with a light orange-red core, whereas 'DrisStrawNineteen' has a flat globose plant habit and dark red fruit with a white core. Additionally, 'DrisStrawFortyEight' has a fruit with a narrow band without achenes, whereas 'DrisStrawNineteen' has fruit with a broad band without achenes.

When 'DrisStrawFortyEight' is compared to the male parent '126R399' (unpatented), 'DrisStrawFortyEight' is a less vigorous plant, with smaller, more conic fruit than '126R399'.

'DrisStrawFortyEight' differs from the commercial variety 'DrisStrawTwentyFour' (U.S. Plant Pat. No. 23,378), in that 'DrisStrawFortyEight' has a globose—semi-upright plant habit and medium-sized fruit that is medium glossy and has a fine texture when tasted, whereas 'DrisStrawTwentyFour' has a flat—spreading plant habit and very large fruit that is strongly glossy and has a coarse texture when tasted.

'DrisStrawFortyEight' differs from the commercial variety 'DrisStrawTwelve' (U.S. Plant Pat. No. 21,538), in that 'DrisStrawFortyEight' has a globose—semi-upright plant habit and medium-sized fruit having a narrow band without achenes, whereas 'DrisStrawTwelve' has a flat plant habit and large-sized fruit having a medium band without achenes.

We claim:

1. A new and distinct variety of strawberry plant named 'DrisStrawFortyEight', substantially as illustrated and described herein.

* * * * *